United States Patent
Comeaux et al.

(10) Patent No.: US 7,104,201 B2
(45) Date of Patent: Sep. 12, 2006

(54) STERILE SURGICAL TABLE COVER

(75) Inventors: Scott A. Comeaux, Castle Rock, CO (US); Sanjay Jatana, Englewood, CO (US)

(73) Assignee: Clear Solutions, Inc., Castle Rock, CO (US)

( * ) Notice: Subject to any disclaimer, the term of this patent is extended or adjusted under 35 U.S.C. 154(b) by 179 days.

(21) Appl. No.: 10/825,451

(22) Filed: Apr. 15, 2004

(65) Prior Publication Data

US 2004/0194673 A1 Oct. 7, 2004

Related U.S. Application Data

(63) Continuation-in-part of application No. 10/644,364, filed on Aug. 20, 2003, now abandoned, which is a continuation of application No. 09/964,182, filed on Sep. 25, 2001, now abandoned.

(51) Int. Cl.
*A47B 13/08* (2006.01)

(52) U.S. Cl. ........................................ 108/90

(58) Field of Classification Search ................ 108/90; 150/158; 5/495, 497; 128/849, 856, 852
See application file for complete search history.

(56) References Cited

U.S. PATENT DOCUMENTS

| | | | |
|---|---|---|---|
| 3,295,577 A | 1/1967 | Danielson | |
| 3,310,091 A | 3/1967 | Geisen et al. | |
| 3,557,856 A | 1/1971 | Berman | |
| 3,729,037 A | 4/1973 | Dare et al. | |
| 3,738,405 A | 6/1973 | Ericson | |
| 3,747,655 A * | 7/1973 | Hadtke | 108/90 |
| 5,069,554 A | 12/1991 | Bonnett | |
| 5,170,804 A * | 12/1992 | Glassman | 128/849 |
| 5,339,748 A | 8/1994 | Bilotti | |
| 5,379,703 A | 1/1995 | Marshall | |
| 5,435,322 A * | 7/1995 | Marshall | 128/849 |
| 5,697,302 A | 12/1997 | Putnam | |
| 5,871,015 A * | 2/1999 | Lofgren et al. | 128/849 |
| 5,896,603 A | 4/1999 | Cooper | |
| 6,116,167 A | 9/2000 | Rabe | |
| 6,205,936 B1 | 3/2001 | Nelson et al. | |
| 6,457,423 B1 | 10/2002 | Gordon | |

FOREIGN PATENT DOCUMENTS

DE 4236160 A1 5/1994

\* cited by examiner

*Primary Examiner*—José V. Chen
(74) *Attorney, Agent, or Firm*—Dorr, Carson & Birney, P.C.

(57) ABSTRACT

A sterile apparatus for covering a surgical tray upon which surgical instruments may be placed. The tray can be covered with a thin flat tubular elongated primary cover which is closed at one end and open at the opposite end. The primary cover is positioned over the tray and any supporting stand and provides a first sterile layer of protection. The invention includes a reinforced secondary cover which is positioned over the primary cover and surgical tray with the outer edges extending under the edges of the tray and drawn firmly toward each other to secure the covers and position them with respect to the tray. This form fit gathers and secures extraneous material from the covers. The secondary cover can include reinforcing layers of additional materials both in the area of the tray as well as the side edges to prevent these areas from being cut or pierced whereby the sterility of the instruments and tray may be jeopardized. Various arrangements are provided for securing the edges of the cover around and under the tray. The primary and secondary covers can be formed together as a one-piece, integral unit to provide a combination sterile barrier. The surface of the tray cover can be partitioned by surface treatment or color coding individual areas for the positioning of certain objects. Flaps can be attached to the perimeter of the cover to temporarily cover certain areas and objects on the tray.

13 Claims, 5 Drawing Sheets

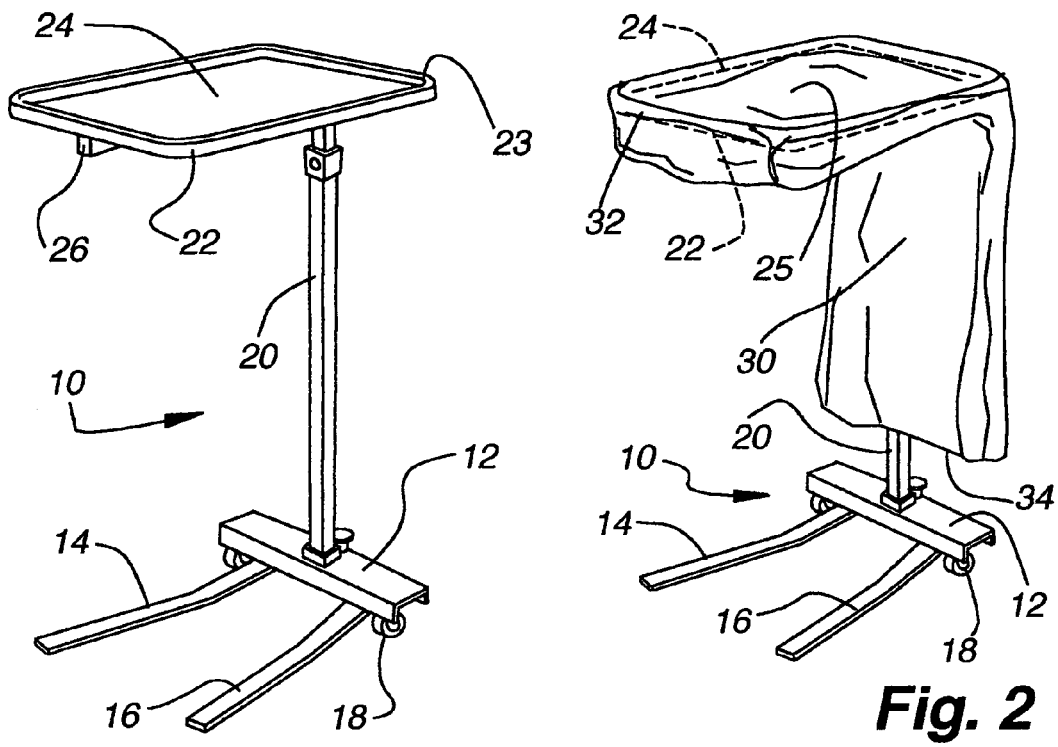
Fig. 1
Prior Art
Fig. 2
Prior Art
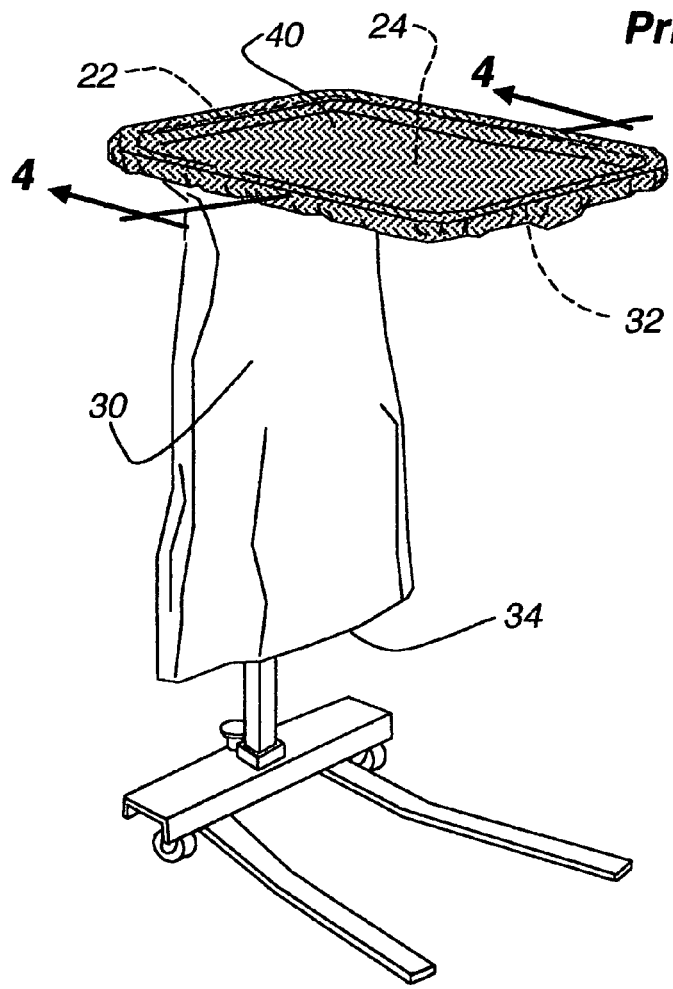
Fig. 3
Prior Art

STERILE SURGICAL TABLE COVER

RELATED APPLICATIONS

This is a continuation-in-part application of U.S. patent application Ser. No. 10/644,364, filed Aug. 20, 2003, now abandoned which is a continuation application of U.S. patent application Ser. No. 09/964,182, filed Sep. 25, 2001, which is abandoned.

BACKGROUND OF THE INVENTION

1. Field of the Invention

The invention relates to a protective sterile cover for a surgical tray used in a medical facility to protect a sterile field for surgical instruments or equipment placed on the tray. More specifically the invention relates to a reinforced secondary cover that is simple to place over a primary tray cover, yielding a sterile and efficient apparatus to protect and maintain the sterile field of the surgical tray.

2. Description Of Prior Art

FIG. 1 shows a typical Mayo stand with tray and FIG. 2 shows a typical cover. The primary or first cover is an elongated flat tubular bag which has a rectangular configuration with one end closed and the opposite end open. The open end is slipped over the tray and provides a very long skirt portion covering the rest of the stand. The cover is held in place merely by gravity. Sterile surgical tray or table covers are essential in operating rooms to provide a barrier between the non-sterile surfaces of medical and surgical trays and supports and the sterile field around the area of treatment, thereby preventing contamination of surgical instruments or other equipment used in surgery by bacteria from outside the sterile field. The drape or cover sits atop a metal tray that the surgical and operating room instruments and equipment are spread upon. Over the first or primary cover on the surgical tray, the surgical nurse or technician historically places two towels to protect the cover and the surgical equipment on the tray from penetrating through the first cover to the surface of the metal tray thus breaking the sterile field barrier. As the towels are in a common flat position, the ends must be tucked under the sides of the tray to present a clean and safe cover of the tray. Any breach of the towels or cover requires the removal of the surgical instruments and recovering the tray with a new primary cover and sterile towels. The towels are tucked under the tray to not leave any drape which could catch on personnel, instruments or interfere with movement.

INFORMATION DISCLOSURE STATEMENT

This section complies with the applicants' requirement to disclose all of the prior art of which they are aware and which may apply to the examination of the present application.

The Erickson Patent (U.S. Pat. No. 3,738,405) discloses a sheath like cover comprising an elongated bag of fabric or plastic sheeting which is pulled over the Mayo stand as well as the support structure. It is initially supplied in a folded and cuffed condition which allows it to be applied to the stand with a minimum of handling to maintain a sterile condition.

The Marshall patent (U.S. Pat. No. 5,379,703) also reveals a folded cover for a Mayo stand and table which includes an elongated flat bag of sterile sheet material which is unfolded at the time of installation and pulled over the table and stand to maintain the sterile condition. This patent is primarily directed to the folding and unfolding of the cover to form an efficient installation.

The Boyt patent (U.S. Pat. No. 5,339,748) discloses a table cover having edges which pass under the edges of the table and are drawn tight by a drawstring positioned within a hem formed along the edge of the cover. The drawstring is used to tighten the cover around the edges of the table in order to hold it in position.

The Rabe patent (U.S. Pat. No. 6,116,167) discloses a cover for a tabletop which is intended to be folded in the middle so that both the top and bottom surface of the table are covered. This patent also discloses that the top surface of the upper portion of the cover includes an anti-slip coating which prevents articles sitting on the tabletop from slipping or falling off. Snaps or straps are shown in use to hold the two halves of the cover in position surrounding the tabletop.

The Cooper patent (U.S. Pat. No. 5,896,603) reveals a cushion article which includes an inwardly extending elastic rim which may be used to overlap the edges of a seat or table to secure the article in place. The article can also have a rubberized web material positioned on the bottom surface to prevent the article from slipping when in contact with the seat or table surface. This patent also describes an article which is formed in two parts having an upper fabric panel and a bottom panel which is a rubberized web. The top and bottom panels are fastened together in an integral configuration whereby the object is held in position against the seat or stool to prevent movement while in use.

The Dare et al patent (U.S. Pat. No. 3,729,037) shows a throw away disposable paper or plastic cover which is formed or molded to conform to the top of a child's highchair tray. Spring clips or cross ties are utilized to hold the bottom edges of the disposable cover under the tray in order to hold the cover in position. The tray also has an upwardly curved outer edge around the perimeter of the tray to prevent the spillage of food or liquids from the tray.

The Burman patent (U.S. Pat. No. 3,557,856) and the Danielson patent (U.S. Pat. No. 3,295,577) show table covers which are held in position around the outer edge of the table surface by means of snaps or Velcro strips.

The Putnum patent (U.S. Pat. No. 5,697,302) merely shows a relatively thick shelf covering for use with wireframe shelves. This patent discloses the use of two separate layers of plastic material which are bonded together either by adhesive or by heat welding so as to form a cover for a shelf which will support objects positioned on the shelf and yet prevent the cover from moving or sliding with respect to its relative position.

SUMMARY OF THE INVENTION

The present invention is a fitted sterile cover for a medical or surgical tray or table and may be made of paper, plastic sheeting, cloth or a combination of two or more of these or similar materials. It is intended to provide a significantly more improved cover than the simple cover and towels previously used for this purpose. It can add significant protection to a simple or primary cover to prevent a breach of the sterile field of the tray. In addition, it has a flat surface that lays over the top area of the tray and a gathered skirt which extends down from the top of the tray.

The invention can be a secondary cover which is secured to the tray by an elastic band, or drawstring, around an outer edge of a skirt, which is part of the cover's design. Thus, the invention can be quickly installed over a primary cover and tray with the gathered skirt fitting under the edges of the tray to gather the excess material of the primary cover to create a form fitting cover that saves time in the placement of the covers and gives uniform and complete coverage of the tray while protecting the instruments that are placed or inadvertently dropped on the tray. The secondary cover can be made from relatively thick material which can reinforce the cover and further protect the tray. In the alternative, additional layers of reinforcing materials can be applied to the secondary cover in the central area and edges of the tray to provide additional protection.

Another embodiment of the present invention includes the above described secondary cover which is at least partially attached to the tray covering area of the primary cover. This attachment can be removable or permanent depending on the intended use of the cover combination. In this way, both covers can be packaged as an integral combination in a sterile container and at the time of use is unfolded and easily slipped over the surgical tray or table with the secondary cover aligned and positioned over the center portion of the tray itself. By merely grasping the outer edges of the secondary cover and pulling the cover edges down over the tray and support stand the cover immediately gathers and ties the outer edges and the loose excess portions of the primary cover underneath the tray and out of the way so that they cannot be snagged or displaced. In this way a form fitting cover surrounds and protects the outer edges of the tray and further protects the surgical tray or table from being touched, cut, pierced or displaced. The combination of the secondary cover precisely positioned and attached to the primary cover provides a compact and efficient product which can be easily and quickly installed over a surgical tray or table with only a few application movements.

OBJECTS AND ADVANTAGES

The objects of the present invention are:

1. To provide a sterile secondary cover for a covered surgical tray which does not use an excess amount of sterile material, thus saving manufacturing costs and storage space.

2. To provide an additional, sterile cover with added substantial protection against penetration for a surgical tray with an extended skirt which does not touch or interfere with the surgical team members, or touch the patient and still gathers all excess material and draping from the primary cover, thus improving safety while at the same time improving the barrier against the breach of the sterile field.

3. To provide consistent, fast and easy secondary and tertiary layers to protect against penetration of the tray sterile field by sharp or heavy instruments.

4. To provide a sterile cover with a skirt which will not touch, and will not be contaminated by, equipment which may be in the operating room.

5. To provided a sterile cover which is securely held on the tray by an elastic band or drawstring, instead of merely by gravity.

6. To provide a sterile cover which cannot be easily removed or dislodged when it is accidentally grasped by the hand of a member of the operating team, or when it is accidentally snagged by a surgical instrument or other object which is being removed from the tray or caught by persons or apparatus that moves around the tray.

7. To provide a secondary protective sterile cover which can quickly adjust to various tables or trays of different sizes and thicknesses because of an elastic band or drawstring or other adjustable gatherer which is part of the cover.

8. To provide an integrated sterile cover with a gathered skirt which will minimize contact with, or be contaminated by, objects in the operating room when the adjustable Mayo stand is lowered toward the operating table.

9. To provide a one-piece integrated sterile cover with a gathered skirt which provides primary and secondary coverage which can be rapidly secured on the tray by a contracting elastic band, drawstring, or gathering device and which can fit various table sizes.

Still further objects and advantages will become evident from the detailed description of the invention, and the drawings which are included herein.

BRIEF DESCRIPTION OF THE DRAWINGS

FIG. 1 is a perspective view of a prior art Mayo stand;

FIG. 2 is a perspective view of a prior art primary sterile cover enveloping the Mayo stand shown in FIG. 1;

FIG. 3 is a perspective view showing a primary sterile cover enclosing the tray or table portion of the Mayo stand and the vertical support member and sterile towels folded over and around the edges of the tray;

DETAILED DESCRIPTION OF THE DRAWINGS

Figure 4:
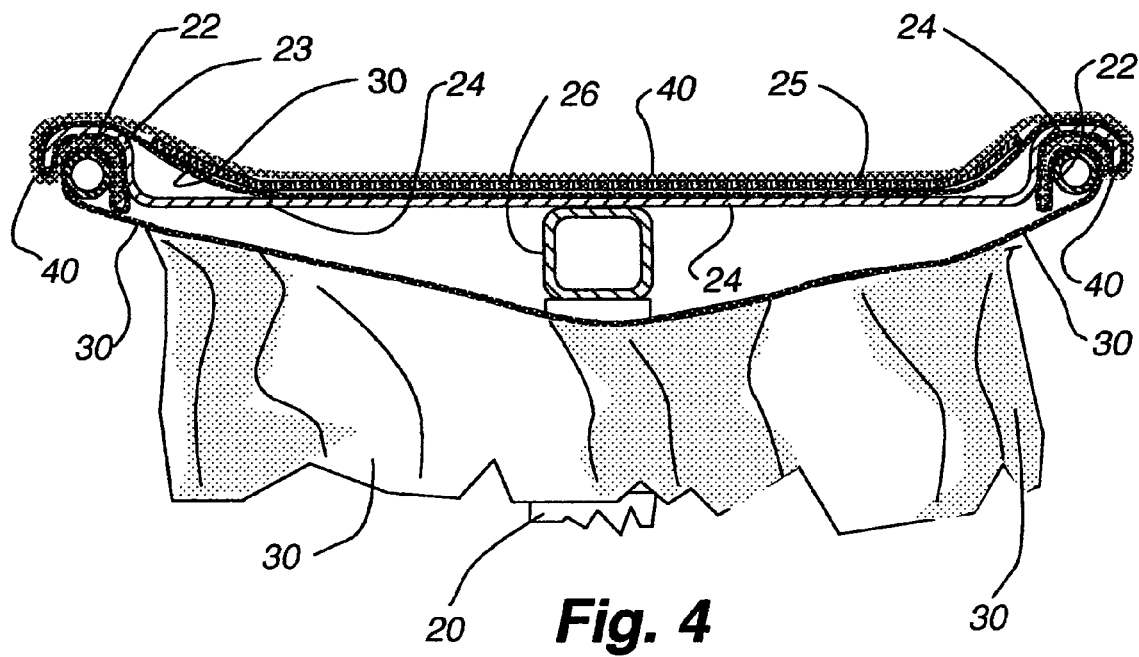
FIG. 4 is a cross-sectional view taken along lines 4—4 of FIG. 3 showing the Mayo stand and primary cover along with the positioned sterile towels as seen in FIG. 3.

Turning now more specifically to the drawings, FIG. 1 shows a typical surgical table or stand 10 which includes a lateral base 12 having outwardly angled support legs 14, 16. The lateral support base 12 can further include casters 18 to aid in easy movement and placement. An adjustable length support member 20 is vertically attached to the base support 12 which, in turn, is permanently attached to a rectangular shaped support ring 22. The support ring 22 supports a flat tray 24 having the same peripheral dimensions as the support ring with an upwardly and outwardly curved edge 23 which allows the tray to be removably supported within the support ring 22. An auxiliary support arm 26 can be provided extending outwardly from the vertical support 20 to provide additional rigidity to the support ring 22.

In FIG. 2, the table or stand 10 is covered with an elongated flat rectangular tubular primary cover 30 which is closed at one end 32 and open at the opposite end 34. The primary cover 30 envelopes the tray 24 and vertical support stand 20.

The purpose of the primary cover 30 which is sterile is used to drape and cover the table 10 as well as the tray 24 and the vertical support member 20 of the table. In this way, a sterile environment or field surrounding the table is provided in the surgical operating room to prevent contamination of the various equipment as well as the instruments which are placed and supported on the surface of the tray 24. The area of the primary cover 30 which coincides with the upper surface of the tray 24 can have a non-skid material 25, such as a foam plastic sheet covering the entire upper or lower surface area associated with the tray. A cover such as this is described in United States patent to R. E. Erickson U.S. Pat. No. (3,738,405). For the purposes of this application, this sterile elongated cover will be called the primary or first cover.

One of the major problems that has taken place in the operating environment is the possibility that this primary cover can be punctured or cut which, in turn, would potentially contaminate the work area as well as the instruments and equipment which are used in an operation. When this situation occurs a major problem exists in that all procedures must cease, all instruments and equipment must be resterilized and the cover for the surgical table must be replaced immediately. This procedure, as can be expected, takes a considerable length of time which puts the life of the patient in jeopardy and adds additional cost to the operation. Any infraction of the sterility provided by the primary cover, thus is a major catastrophic situation in the operating room environment.

To help protect against this type of catastrophe in the prior art, sterile towels 40 are wrapped around the surgical tray 24 forming part of the stand 10. Since the tray 24 is merely supported by the support ring 22 the edges of the towels 40 are tucked under the sides of the tray and somewhat hold the excess materials of the primary cover 30. The fullness of the primary cover 30 with respect to the dimensions of the tray 24 sometimes provides a problem since this excess material can be caught or pulled which can dislodge or misplace some of the instruments and the positioning of the tray itself. The use of sterile towels 40 does not eliminate or solve this type of problem which can occur even with the sole use of the primary cover 30 itself.

Figure 5:
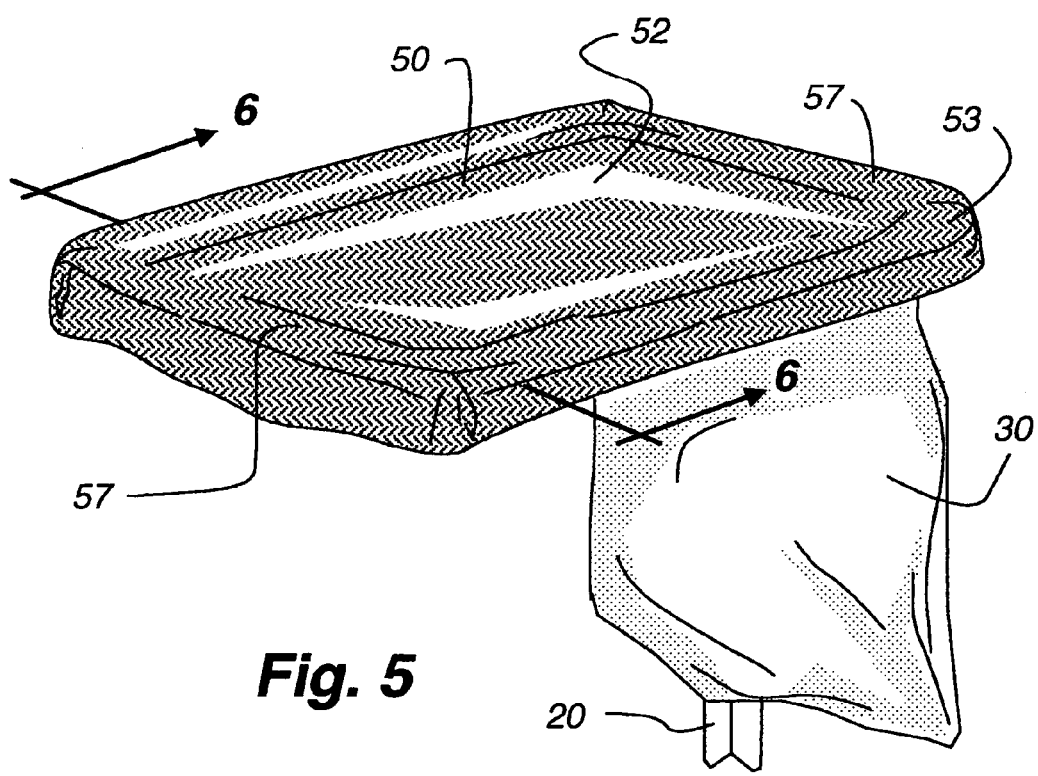
FIG. 5 is a perspective view of the Mayo stand along with the primary sterile cover with a secondary cover according to the present invention positioned over and holding the primary cover around the edges of the Mayo tray or stand.
Figure 6:
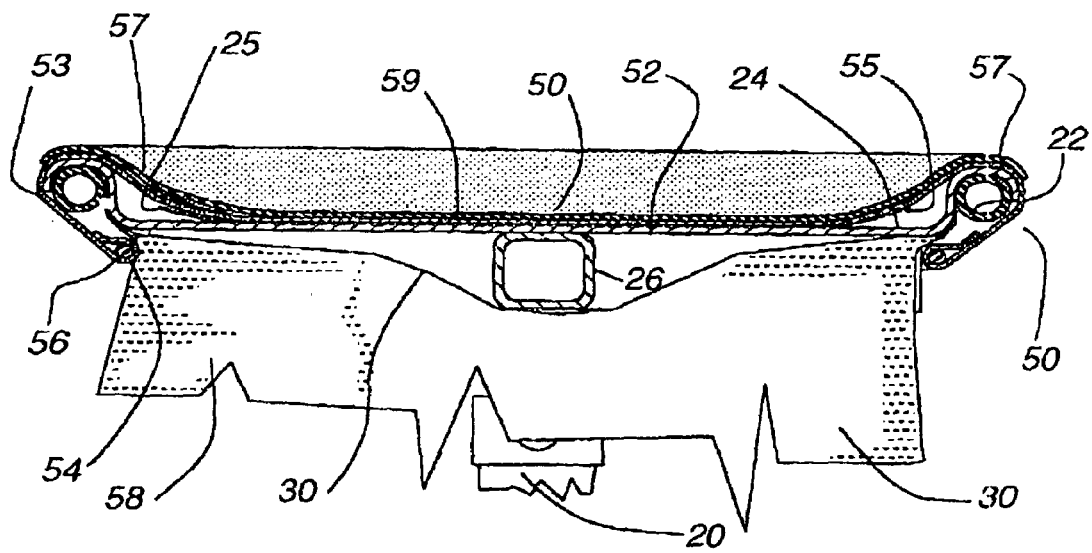
FIG. 6 is a cross-sectional view taken along lines 6—6 of FIG. 5 showing the primary cover draped over the tray of the Mayo stand with the form fitted secondary cover positioned over and surrounding the tray and supporting the excess material of the primary cover.
Figure 7:
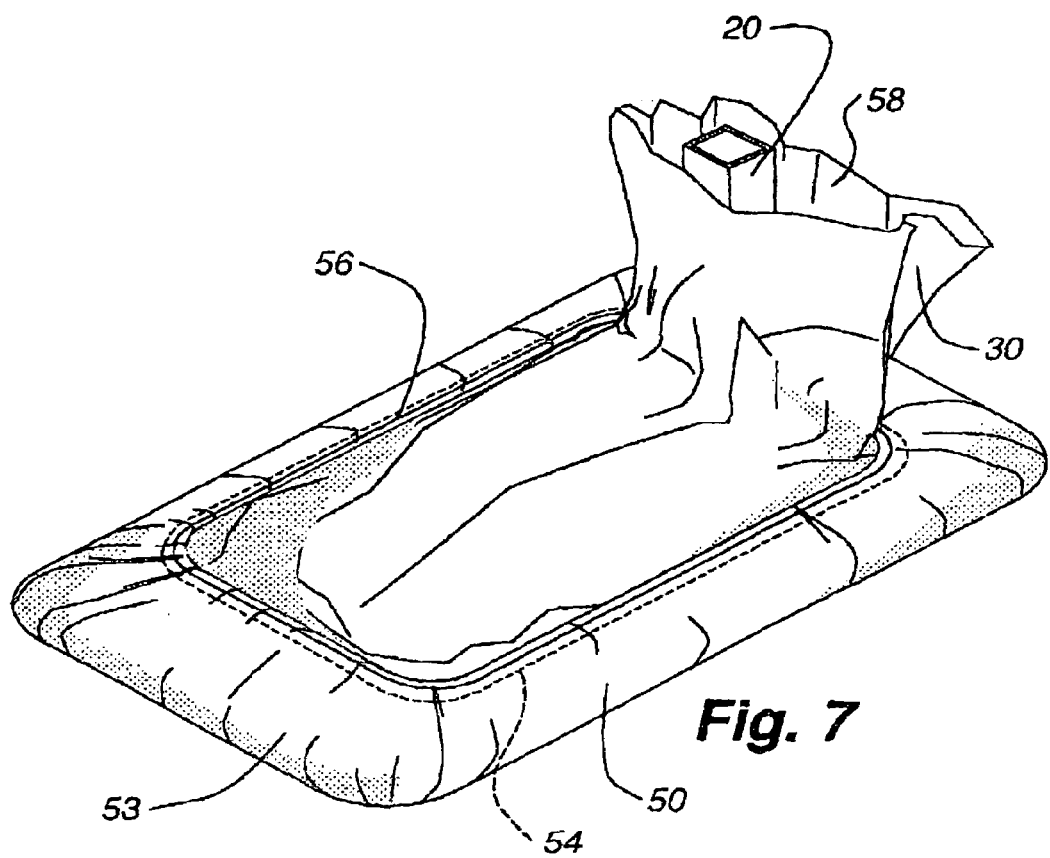
FIG. 7 is a bottom perspective view showing the gathered outer edges of the secondary cover surrounding the primary cover and the tray and support member.
Figure 8:
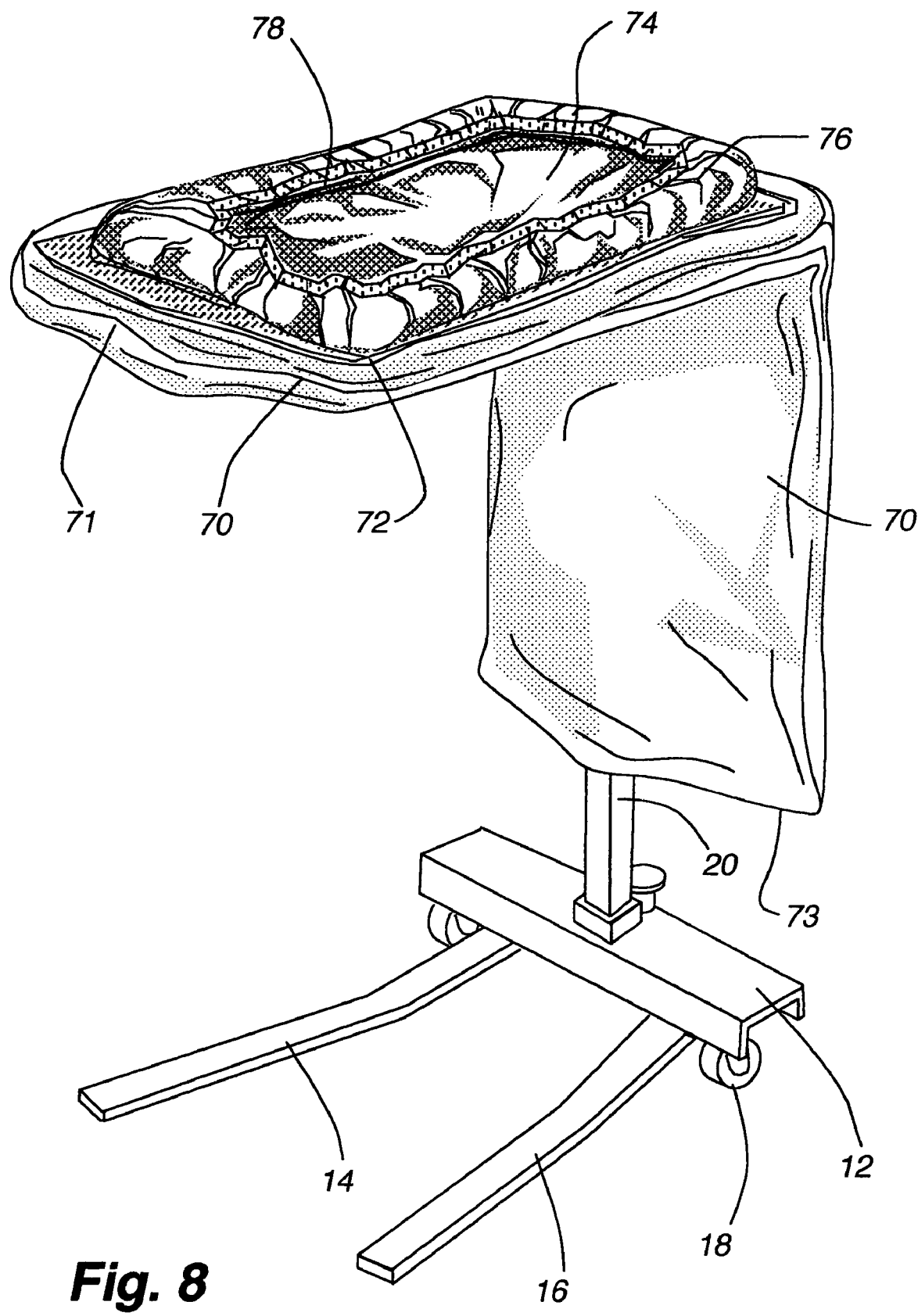
FIG. 8 is a perspective view showing the Mayo stand with a combination primary and secondary sterile cover positioned over the tray before the installation of the fitted secondary cover.

FIGS. 5–7 show the present invention which is a sterile cover 50 that can be used in conjunction with the primary cover 30 to provide additional reinforcement and protection to the table area during use in the operating room. The secondary cover 50 has an outer perimeter area or skirt 53 that substantially coincides with the outer peripheral area and dimensions of the tray 24 in the stand 10. Thus, the sterile secondary cover 50 includes a center tray covering section 52 and a side skirt portion 53 which is sewn or attached to the outer perimeter of the center section 52 or is a continuation of the existing material forming the center section 52. A tensioning or gathering device 54, such as an elastic band or thin helical spring can be encased in the hem 56 around the perimeter of the edges of the secondary cover 50. In this way, as seen in FIG. 7 the sterile * secondary cover is positioned over and surrounds the tray 24 as well as the support ring 22 of the surgical table or stand 10. The tensioned edge or hem 56 along the edge of the cover 50 pulls the edges relatively tight or snug around the underside of the tray and thus encases the excess or surplus material that exists in the primary cover 30.

The downward skirt 58 of the primary cover 30 is also gathered and positioned closer in proximity to the vertical support member 20. In this way the primary cover 30 of the surgical stand 10 is fitted around the tray 24 as well as the vertical support member 20 to eliminate and control the excess material which is present in the primary cover 30. This greatly reduces the possibility of the primary cover 30 being caught or shifted which could, in turn endanger the sterility of the surrounding area.

The side skirt area 53 of the secondary cover 50 can be reinforced with additional layers of material 57 which can coincide again with the tray itself or as shown in FIG. 6 can extend over the edges of the tray to provide additional protection and reinforcement. The protective layer 57 that is positioned on the upper surface of the secondary cover 50 in the vicinity of the center area of the tray 24 can be of a type of material that is not easily penetrated or cut and also is impervious to fluids. This material also can be a non-slip or non-skid type material to prevent the easy movement or sliding of instruments and equipment along the surface of the tray covered by the secondary cover 50. It is desirable that this material be extremely strong, such as Kevlar, but still flexible enough that it can be folded and packaged in a sterile condition for storage. It is also understood that any type of tensioning device can be used to tension and gather the edges 56 of the secondary cover 50 which will help to gather it and retain the tight fit of the cover surrounding the surgical tray 24. The use of the secondary cover 50 is quite important from the standpoint of protection to the primary cover 30 and the surgical stand or table 10 to prevent the breach of the sterile condition which is an essential for the support of surgical appliances, instruments and equipment during any sterile operating procedure.

It is anticipated that the secondary cover 50 will have a side skirt member or members 53 which can be approximately 2–6 inches in width to provide sufficient material so that the tensioning device 54 provided in the hem or edge 56 of the cover will create a secure closure along the bottom of the tray. It is important, however, that the side skirt 53 be short enough so that it does not hang down from the stand which would in any way contact an object beneath the stand. The required tensioning device 54 can also be belts and snaps, a lateral elastic band or Velcro type fasteners which are arranged to sufficiently support and tighten the outer edges 56 of the secondary cover 50.

In use the primary cover 30 is unfolded from its sterile packaging and pulled over the tray 24 and support ring 22 and then draped downwardly over the vertical support 20 until the closed end 32 of the primary cover 30 is tight against the outer edge of the tray 24. Next, the secondary cover 50 according to the present invention is removed from its sterile package and is unfolded in a position with the outer surface of the cover 50 and reinforcing layer 57 facing upward on the center of the tray 24. In this position the outer skirt edges 53 are then rolled outward and downward along the outer edges of the perimeter of the tray 24 with the hemmed edges 56 and tensioning device 54 rolled over and under the outer edges of the tray. This rolling motion created by the application of the secondary cover 50 gathers and pulls the surplus material of the primary cover 30 so that it is held under and in close proximity to the undersurface of the tray 24 of the Mayo stand 10. At the same time this gathering created by the tensioning edge 54, 56 of the secondary cover 50 around the vertical support member 20 causes the elongated skirt portion 58 of the primary cover 30 to be gathered into close proximity with the support 20.

It is to be understood that the center top portion of the secondary cover 50 which corresponds with the flat surface of the tray 24 can have any rectangular dimensions required to match different sizes of trays, tables or stands which are commonly used in an operating room environment. It is also to be understood that the protective secondary cover which is shown and described in this application can also be used in other areas or locations in which sterility for a surgical procedure is required. Although it is intended that the secondary cover shall be used as reinforcement and protection for the conventional primary cover used in conjunction with support areas, such as the surgical stand, the secondary cover can also be used by itself with other stands or tables since it provides a complete sterile field and support for instruments and equipment used during any procedure.

The secondary cover according to the present invention can be fabricated from one single piece of flexible sheet material or can be sewn or formed with a number of individual pieces which are attached to each other to form the required dimensions of the secondary cover. It can be formed from any suitable sheet like flexible material, such as sterile paper, cloth, polyethylene or other similar flexible plastic films. The cover can be sterilized by common and conventional appropriate methods and is then packaged in a sterile environment. In this way a secondary reinforcement and protective sheath can be provided for maintaining and preventing breach of the sterile field of a stand either with or without the primary elongated baglike cover. It is also possible to provide a non-slip layer of material on the bottom surface of the secondary cover 50 which corresponds with the surface of the tray 24 to aid in the prevention of slippage of the cover with the handling and movement of the surgical instruments or equipment.

The tensioning device 54 for closure beneath the tray of the skirt portion 53 of the secondary cover 50 can include in addition to or instead of elastic bands and drawstrings, hooks and fabric strips, such as Velcro, or plastic or metal snaps, buttons, hooks, eyelets, belts and buckles or any similar securing device which will provide a satisfactory result. In addition, the outer surface of the secondary cover 50 can be coated with plastic, rubber, water-repellant chemicals, etc. in order to provide a moisture impervious barrier.

Figure 9:
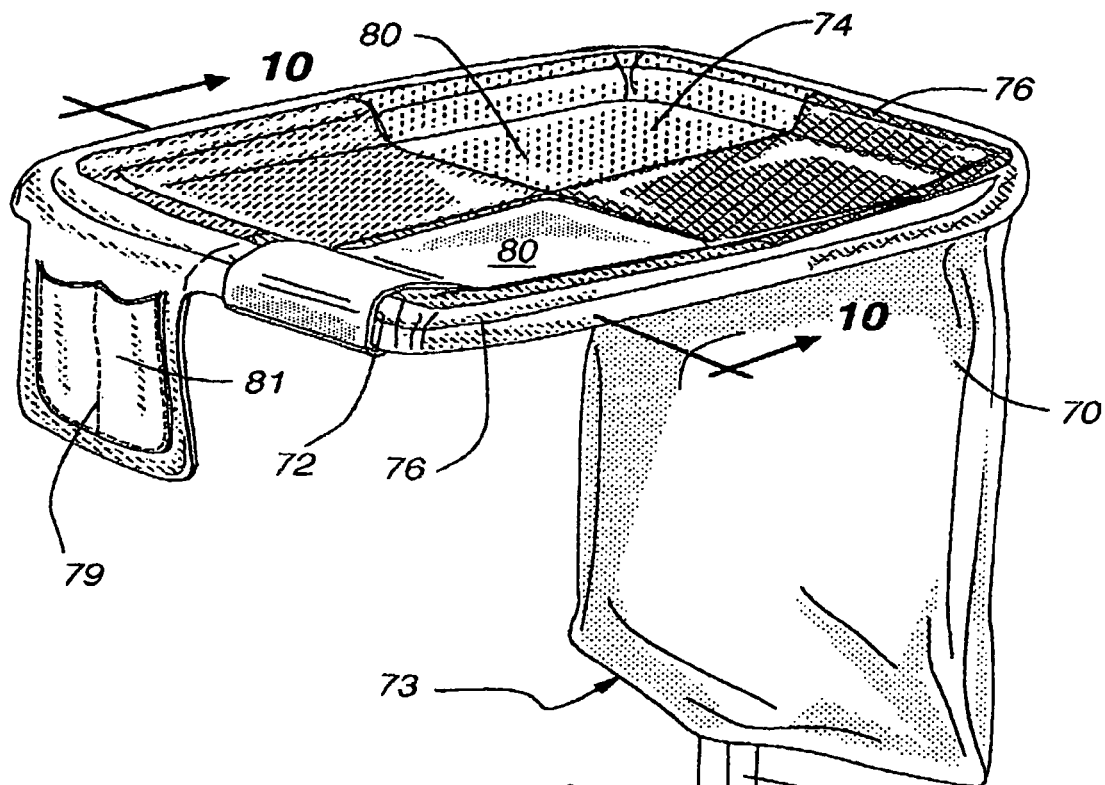
FIG. 9 is a perspective view of the Mayo stand and combination cover shown in FIG. 8 with the secondary cover installed showing partitioned surface areas on the tray portion of the cover with folded suspended flaps attached along the perimeter of the secondary cover for covering and protecting sterile equipment and instruments positioned on the tray.
Figure 10:
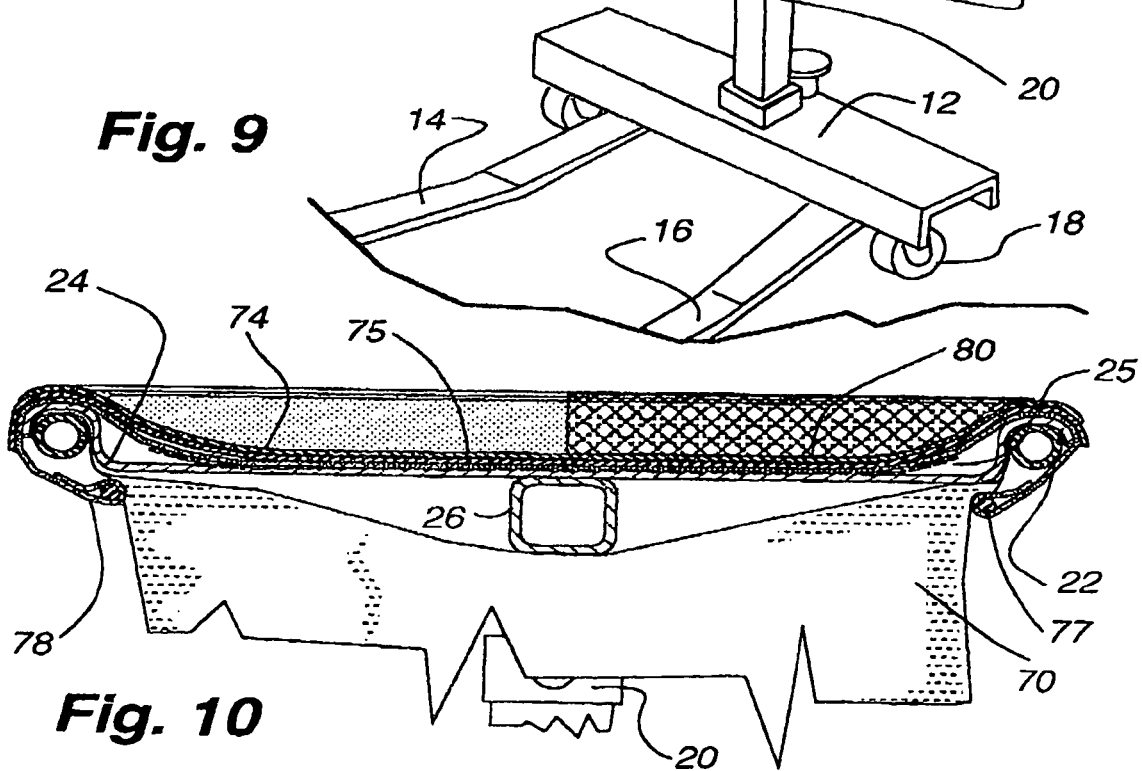
FIG. 10 is a cross-sectional view taken along lines 10—10 of FIG. 9 showing the cross-section of the installed combination cover.

FIGS. 9 and 10 show another embodiment of the present invention wherein the primary sterile surgical covering 30 and the secondary sterile protective cover 50 are integrated in a combination cover that provides all of the desirable characteristics of the two individual covers.

In this arrangement an elongated rectangular flat bag-type enclosure or first cover 70 closed at one end 72 and open at the opposite end 73 is provided. This enclosure 70 is designed to be installed and slipped over the tray and support of a surgical stand to enclose and cover the tray 24, the support ring 22, as well as the vertical support member 20. One portion of the enclosure 70 with its closed end 72 in juxtaposition with the outer edge of the tray 24 has a flat upper surface area 75 which corresponds with the area of the support tray 24. A second cover 74 of flexible sheet like material is attached or adhered to this corresponding upper surface 75 of the enclosure or cover 70. This second sheet like cover 74 has an outwardly extending skirt 76 which extends outwardly beyond the outer perimeter of the tray 24. The outer extending edges of the skirt 76 are gathered by a tensioning device 77, such as an elastic cord or spring formed within a hem 78 formed around the outer perimeter edges of the skirt 76. The sterile enclosure 70 is positioned over the surgical stand or tray so that the closed end 72 of the enclosure 70 is in contact with the outer edge of the tray. The upper layer of the flexible second cover 74 including the outer skirt 76 and tensioning device 77 is properly positioned to coincide with the tray 24. The outer edges of the skirt 76 along with the tensioning device 77 are stretched so that the outer skirt 76 can be pulled or rolled outward and downward around the outside edges of the tray 24 as shown in FIG. 9. In this way, a sterile reinforced combination cover can be provided for a surgical tray that will endure considerable use and abuse. One or more layers of additional material 80 can be applied to the upper surface of the flexible second cover so as to provide additional reinforcement and protection as required.

An additional feature of the present embodiment can be the dividing of the top surface of the tray portion of the flexible second cover 74 into various partitions. The partitioning can be in the form of various surface designs or texture or the application of various colors to the partitions on the surface of the tray. The purpose of the partitions or different color coded areas is so that the positioning of various instruments can be allocated to certain areas or locations to segregate various types of instruments or equipment. In this way, the assistants or surgeons know intuitively in what areas the required instruments are located rather than having to peruse the entire surface area of the tray to find the desired item.

In addition, to further protect the cover and the sterility of the surgical tray one or more flaps 79 can be attached to the outer edge of the skirt portion of the flexible second cover with a desired size and position to be folded over the surface of the tray to cover various portions of the tray. In this way various areas can be protected from contact by hands or other equipment or instruments during the course of use. The flaps 79 can also have pockets 81 formed on the outer surface of the flap 79 for storage or support of instruments when the flap is suspended downward. Once the instruments or equipment under a particular flap are required then that flap can be easily pulled back over the edge of the cover so as to be suspended downward. One or more of flaps 79 can be strategically located around the perimeter of the cover and can have any size desired to cover or protect a specific area. When a flap 79 is folded over the cover and possibly instruments, additional instruments can be laid on top of the flaps to further segregate instruments on the tray.

As seen in this application it is critical in any type of surgical operation or procedure that the sterility of the environment, especially in that area which is in contact or supporting various instruments or equipment which are used during the operation, shall be maintained. The breach of the sterility of the support stand or tray necessitates and demands protection which can guarantee with certainty that the sterile environment and barrier will be maintained at all times. The present invention is directed specifically to a reinforced cover which can be provided as a barrier cover or an addition to a primary cover to maintain and protect the support area at all times. The present invention provides that protection and that additional extra measure of assurance that the sterility of the support stand or tray and the instruments thereon will not be in any way questioned or jeopardize the integrity of any surgical procedure. The covers of the present invention provide that security greatly reducing the overall potential costs that can be associated with this type of procedure.

In the combination embodiment, the primary layer can be a thin flexible polyethylene or a polyurethane plastic sheet material or the like while the upper flexible cover can also be a plastic sheet material or paper or rubber or any other suitable sheet material which provides the desired flexible and impermeable characteristics. The reinforcing layer on the upper surface of the flexible cover can be an extremely dense plastic or synthetic material which is not easily penetrated or cut, such as the cutting sheets that are presently produced by S. C. Johnson and Son, Inc., under the SARAN trademark. It is also possible that a thin sheet of KEVLAR or other similar material could be used for this purpose since its high strength characteristics are well known.

ALTERNATIVE EMBODIMENTS

The invention can be made so that the flat top surface member 52 has different rectangular dimensions to match different sizes of trays or stands. The flexible material for the cover can be sterile paper, cloth, polyethylene, or similar flexible plastic films. The invention could be sterilized by common and appropriate methods. The invention can also be made from one piece of flexible sheeting with a drawstring or elastic band around its perimeter instead of being made from two or more pieces. If seams are used, the flat top surface member 52 can be connected by top side seams to the side skirt member 53. This version would be easier and cheaper to make and would fit tabletops of varying sizes. Such one-piece cover may have a quasi rectangular shape adaptable to a variety of sizes of tables or stand tops.

It is also possible that partitions and flaps as explained in the combination cover could also be provided with the previously described individual secondary cover.

CONCLUSIONS, RAMIFICATIONS AND SCOPE

For use in cases where the stand or table can not be completely sterilized, the cover material of the invention may be waterproofed by various methods, such as coating with plastic, rubber, water repellent chemicals, etc. In situations where it is desired that the flat top surface member 52 should not slip against the top of the tray of the stand, the underside of the top surface member 52 can be coated with non-slip rubber-like material 55 known to those skilled in the art. Likewise, the top surface member 52 can have a similar non-slip surface 59 on the outside surface so that surgical instruments placed on the top surface member 52 will not easily move across the surface. To withstand the weight of very heavy or sharp instruments or objects placed on the top surface member 52, the material of the invention can be reinforced by lamination 57 with a tough plastic or woven fabric layer along the outer rim or edge or over the entire surface. The means for attaching the side skirt member 53 to the flat top surface member 52 may include gluing, stitching, heat welding or other means known to those skilled in the art.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. A reinforced cover apparatus for providing a sterile environment for a surgical tray, the surgical tray having an upper and lower surface and an outer peripheral edge, the apparatus comprising:

a) a first cover formed from flexible sheet material in an elongated tubular configuration having a closed end and an opposite open end; the open end of said first cover being installed over said tray by passing said first cover over the tray until the closed end of the cover is in contact with said tray, said first cover when in said position having a support area which corresponds with the upper surface of said surgical tray:

b) a second cover formed from a flexible material and having a configuration corresponding to said support area of said first cover and an outer peripheral edge, said second cover includes securement means which holds the second cover over the first cover and said surgical tray so that both covers are securely held in position on said tray and any excess material of said first cover is gathered and held in close proximity to the lower surface of said surgical tray to prevent the covers and tray from being unintentionally caught and the tray displaced.

2. A reinforced cover apparatus as defined in claim 1 wherein the securement means of said second cover includes an outwardly extended skirt portion which is attached to the outer peripheral edge of said second cover, said skirt portion has an outer second edge which includes a tensioning means attached to the second edge so as to hold the second and first covers securely in position over said surgical tray.

3. A reinforced cover apparatus as defined in claim 2 wherein said securement means includes an elastic strip formed within a hem formed around the second edge of said skirt portion of said second cover.

4. A reinforced cover apparatus as defined in claim 1 wherein the securement means of said second cover includes a tensioning means provided in conjunction with the outer peripheral edge of said second cover.

5. A reinforced cover apparatus as defined in claim 1 wherein the configuration of said second cover is sufficiently large so as to allow the second cover to at least partially overlap the outer peripheral edge of said surgical tray.

6. A reinforced cover apparatus as defined in claim 5 wherein the second cover includes a reinforcement layer in the area corresponding to the upper surface of said surgical tray which prevents the covers from being cut or punctured which would compromise the sterile environment of the tray.

7. A reinforced cover apparatus as defined in claim 6 wherein the reinforcement layer is attached to the second cover and is sufficiently large to overlap the outer peripheral edge of said surgical tray.

8. A reinforced cover apparatus as defined in claim 7 wherein an outer surface of said reinforcement layer includes a non-skid coating which reduces accidental movement of instruments or equipment positioned on said surgical tray.

9. A reinforced cover apparatus as defined in claim 1 wherein said first and second covers are sterilized by a suitable process to provide a sterile environment for said surgical tray.

10. A reinforced cover apparatus as defined in claim 1 wherein said second cover and said first cover are permanently joined together to form the reinforced cover apparatus in an integrated one-piece unit.

11. A reinforced cover apparatus for providing a sterile environment for a surgical tray having an upper and lower surface area and an outer peripheral edge, said apparatus comprising:

a) a first cover formed from flexible sheet material in an elongated tubular configuration having a closed end and an opposite open end, said first cover being installed over said tray by passing the open end of said first cover over the tray until the closed end is in contact with said tray, said first cover when installed having a support area which corresponds to the upper surface of said surgical tray;

b) a second cover formed from a flexible material and having a configuration corresponding to said support area of said first cover and an outer peripheral edge, said second cover including a securement means which holds the second cover over the first cover and said surgical tray so that both covers are securely held in position on said tray and any excess materials of said first cover is gathered and held in close proximity to the lower surface of said surgical tray; and c) said first cover and said second cover are at least partially attached in the support area of said first cover whereby the first and second covers form an integral one-piece unit which can be installed over said surgical tray in a combined single installation.

12. A method of providing a sterile environment for a surgical tray which includes the steps of;

a) installing a first sterile cover formed from a flexible sheet material in an elongated tubular configuration having a closed end and an opposite open end;

b) moving said open end of the first cover over said tray until said closed end of said first cover is in contact with an edge of said tray;

c) positioning a second cover over said first cover so that said second cover corresponds to an upper surface of said surgical tray; and d) pulling the edges of said second cover down and under the surgical tray and tensioning the edges of said second cover so as to tightly gather any excess material of said covers so as to hold the edges of the covers firmly against the under surface of said surgical tray so that the covers and tray can not be unintentionally caught which could displace said tray.

13. A method of providing a sterile environment for a surgical tray as defined in claim 12 which further includes the step of permanently adhering the first and second covers in the area corresponding to the upper surface of said surgical tray so that they form a single integrated one-piece unit.

* * * * *